(12) United States Patent
Noble et al.

(10) Patent No.: US 6,709,451 B1
(45) Date of Patent: *Mar. 23, 2004

(54) CHANNELED VASCULAR STENT APPARATUS AND METHOD

(75) Inventors: Lawrence E. Noble, Scottsdale, AZ (US); Jeffrey A. Miller, Chompson, OH (US)

(73) Assignee: Norman Noble, Inc., Cleveland, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/616,274

(22) Filed: Jul. 14, 2000

(51) Int. Cl.[7] .................................................. A61F 2/06
(52) U.S. Cl. ...................................... 623/1.15; 623/1.42
(58) Field of Search ..................... 623/1.15, 1.42–1.46, 623/1.39, 1.4, 1.23, 904; 427/2.24

(56) References Cited

U.S. PATENT DOCUMENTS

| | | | | |
|---|---|---|---|---|
| 4,307,723 A | | 12/1981 | Finney | 128/349 R |
| 5,591,197 A | * | 1/1997 | Orth et al. | 623/1.15 |
| 5,681,345 A | * | 10/1997 | Euteneuer | 623/1.15 |
| 5,718,713 A | | 2/1998 | Frantzen | 606/198 |
| 5,769,883 A | * | 6/1998 | Buscemi et al. | 623/1.15 |
| 5,843,172 A | | 12/1998 | Yan | 623/1 |
| 5,860,999 A | | 1/1999 | Schnepp-Pesch et al. | 606/194 |
| 5,873,904 A | * | 2/1999 | Ragheb et al. | 623/1.15 |
| 5,879,370 A | | 3/1999 | Fischell et al. | 606/198 |
| 5,882,335 A | | 3/1999 | Leone et al. | 604/96 |
| 5,891,108 A | | 4/1999 | Leone et al. | 604/264 |
| 5,972,027 A | * | 10/1999 | Johnson | 424/422 |
| 5,989,207 A | | 11/1999 | Hughes | 604/8 |
| 6,071,305 A | * | 6/2000 | Brown et al. | 606/191 |
| 6,132,461 A | * | 10/2000 | Thompson | 623/1.15 |
| 6,190,404 B1 | * | 2/2001 | Palmaz et al. | 623/1.15 |
| 6,253,443 B1 | * | 7/2001 | Johnson | 623/1.15 |
| 6,254,632 B1 | * | 7/2001 | Wu et al. | 623/1.15 |
| 6,273,913 B1 | * | 8/2001 | Wright et al. | 623/1.42 |
| 6,379,381 B1 | * | 4/2002 | Hossainy et al. | 623/1.15 |

FOREIGN PATENT DOCUMENTS

| | | | | |
|---|---|---|---|---|
| DE | 199 06 956 A1 | 8/2000 | | A61F/2/04 |
| WO | WO 99 23977 A | 5/1999 | | A61F/2/06 |

* cited by examiner

*Primary Examiner*—Michael J. Milano
*Assistant Examiner*—(Jackie) Tan-Uyen T. Ho
(74) *Attorney, Agent, or Firm*—Mayrocki, Rooney & Siverton, P.A.

(57) ABSTRACT

A vascular stent having one or more channels in the outer surface. The channel(s) provide increased flexibility, enhanced perfusion, increased chronic positional stability, and convenient dispensing of a medication. Preferably the stent is machined into a mesh-like pattern and the channel(s) are machined into the stent elements of the pattern. The channels may be oriented in a variety of ways. Parallel orientation tends to provide greater enhancement of perfusion whereas perpendicular orientation provides differential flexibility. For greater control of differential flexibility, the channel may be further machined in the stent element, producing a regain of greater flexibility.

17 Claims, 9 Drawing Sheets

CHANNELED VASCULAR STENT APPARATUS AND METHOD

CROSS REFERENCE TO CO-PENDING APPLICATIONS

None.

BACKGROUND OF THE INVENTION

1. Field of the Invention

The present invention generally relates to medical devices, and more particularly relates to devices for reinforcement of a portion of a vascular wall.

2. Description of the Prior Art

It is well known in the prior art to design and build apparatus for the treatment of various vascular disorders. It is common to group these therapies in accordance with the location within the body of the vessel(s) to be treated. For example, peripheral vascular therapies treat vascular disease of the extremities. Similarly, cardiac vascular therapies treat vascular disease of the coronary system. This method of differentiation is particularly helpful in that the medical procedures and corresponding medical devices tend to be specifically tailored to the individual application.

The primary disease effecting the coronary system involves the build-up of material within the lumen of a vessel which partially or completely occludes the vessel preventing adequate perfusion. Though there are reported attempts in the literature to provide treatment using systemic drugs, the primary therapies involve invasive procedures.

Perhaps most common, is the by-pass surgical procedure. Most typically this involves a complete tracheotomy during which those sections of the coronary arteries which are partially or completely occluded are surgically removed. If the occluded sections prove to be quite long, it may be necessary to supply artificial or organic graft material. Common artificial grafts are made from woven polymer fibers. Natural grafts may be transplanted from a human or animal donor or may be harvested from the patient, as with the use of the patient's saphenous vein.

The key alternative to by-pass surgery is a less invasive procedure termed percutaneous translumenal coronary angioplasty (PTCA). In this procedure, a catheter is inserted percutaneously into an artery (usually the femoral artery in the leg) and advanced so that the distal portion, containing an inflatable balloon reaches the occluded section of the coronary artery. Inflation of the balloon compresses the occluding material into the vessel wall, thus increasing the effective cross section of the vessel. Because the procedure is much less invasive than by-pass, it is much less costly and much less traumatic.

However, the prevalent medical concern about PTCA involves the restenosis rate. A number of preliminary studies have shown that the rate at which treated vessels subsequently reocclude may be unacceptably high. The exact mechanism whereby restenosis occurs is not well understand, notwithstanding considerable on-going research on the topic. Yet, it seems rather intuitive that the vessel wall, in the region of the initial lesion, may have been weakened by the disease. It also seems likely that such a weakened vessel wall may indeed be further weakened by the PTCA procedure, itself.

Thus, it has become a common practice to supplement the PTCA procedure with the implantation of a stent to provide reinforcement of the vessel wall. A stent is a generally cylindrical structure which fits snugly the inside dimension of the inner vessel wall, providing additional radial strength against restenosis. U.S. Pat. No. 4,307,723, issued to Finney, describes a stent having a considerably different configuration which is commonly utilized within the urinary tract.

U.S. Pat. No. 5,989,207, issued to Hughes, shows a relatively elongate stent structure. A stent more specifically configured for coronary use is seen in U.S. Pat. No. 5,879,370, issued to Fischell et al. Frantzen, in U.S. Pat. No. 5,718,713, describes a stent structure produced of a mesh having a flattened outer surface. U.S. Pat. No. 5,843,172, issued to Yan describes a stent which is porous to provide chronic release of a drug. With all of these proposed stent structures, there remain the concerns of accomplishment of the basic purpose of the stent implantation, without undue chronic movement and without undue prevention of the perfusion of the endothelial cells of the stented vessel wall.

SUMMARY OF THE INVENTION

The present invention overcomes many of the disadvantages found in the prior art by offering a method of and apparatus for providing the desired stent functions yet having improved properties of placement and chronic implantation. These improvements are derived from the fabrication techniques and physical configuration of the stent of the present invention.

The present invention offers a greater opportunity for positioning and dispensing of medication for chronic drug therapy. It also provides enhanced chronic retention, improved perfusion, and differential flexibility in placement.

In the preferred mode of practicing the present invention, the stent is fabricated from hollow, cylindrical, tube-like stock of a biocompatible material, such as titanium or medical grade stainless steel. The raw stock is preferably "machined" on a machine tool having a rotary laser cutting head, which cuts a mesh-like pattern through the wall of the metal stock. It may be appropriate, in certain other applications, to utilize a memory-type metal, such as Nitinol.

In addition to the pattern cut entirely through the stock, one or more pockets or channels are cut into but not through the stent wall. These pockets or channels can greatly enhance the positional stability of the stent, because the channel edges tend to more tightly grip the vessel wall. The pockets or channels can incidentally provide a path for blood flow between the outer stent wall and the endothelial cells of the inner vessel wall. As a result, the present invention can provide enhanced perfusion of the stented vessel wall. This enhanced perfusion would especially benefit stent designs having an embedded medication, because it would generate greater distribution of the drug.

The pockets or channels may be machined circumferentially or longitudinally with respect to the normal blood flow. Longitudinal orientation would tend to provide the greatest enhancement of perfusion. This will be the configuration for many applications.

Circumferential orientation of the pockets or channels provides all of the above described benefits and also imparts differential flexibility along the length of the stent. This occurs because the reduced metal of the pocket or channel more readily permits a bend to occur at the location of the channel. This differential flexibility is particularly useful in effective placement of the stent, although it is also helpful in positional retention around bends in the vessel wall.

One particular embodiment of the present invention provides for differentially machining a stent mesh pattern at one or more selected locations. These breaks are useful for imparting a particular desired degree of differential flexibility.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
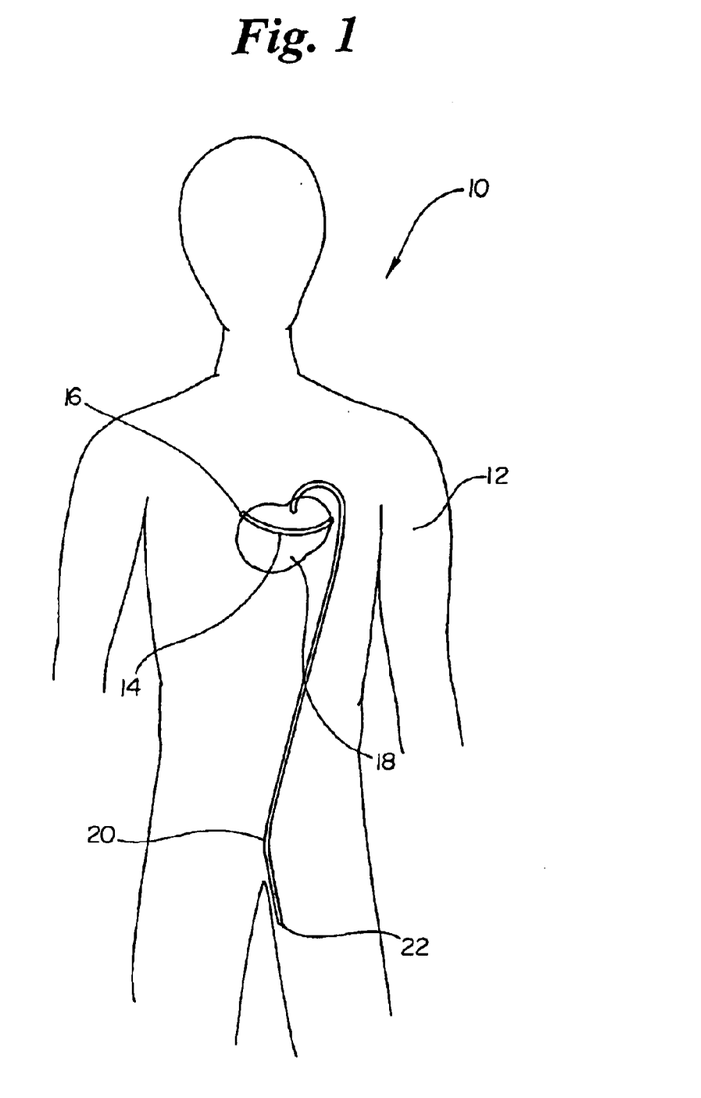
FIG. 1 is a diagram schematically showing the overall medical procedure.

FIG. 1 is a diagram 10 schematically showing the overall medical procedure. Patient 12 has experienced occlusion 14 of coronary artery 16. This has caused insufficient perfusion to myocardial tissue 18 of patient 12. To conduct the PTCA procedure known in the art, the distal portion of a catheter containing a dilation balloon and stent is percutaneously inserted at incision 22 and advanced through artery 20 into coronary artery 16 to occlusion 14. Occlusion 14 is opened and stented in the manner known in the art.

Figure 2:
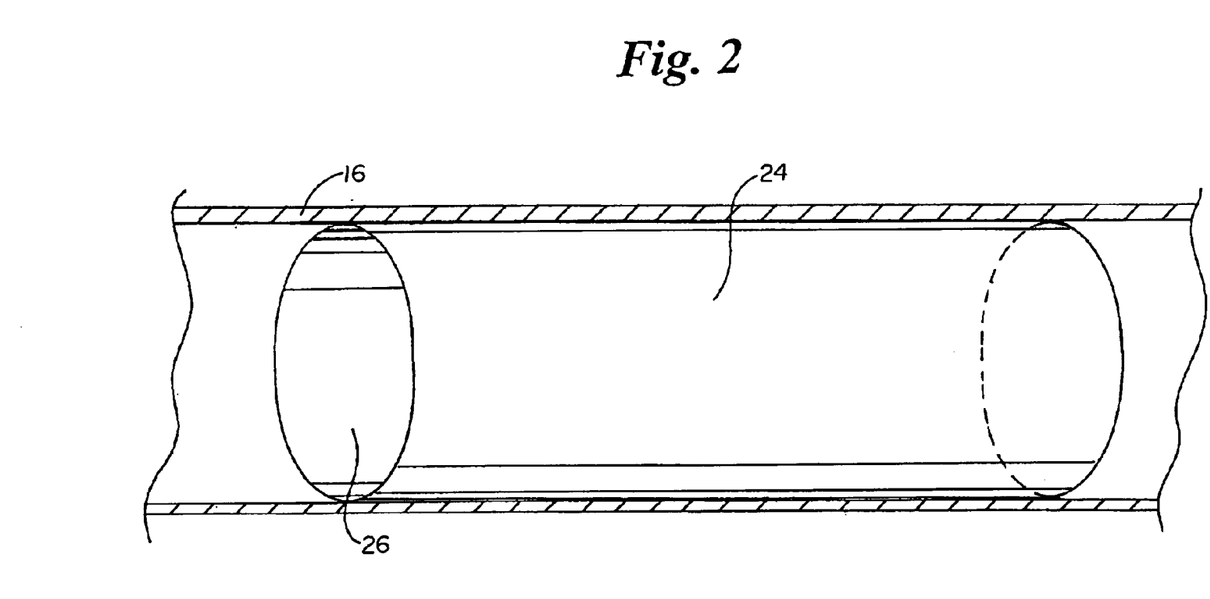
FIG. 2 is a closeup view conceptually showing the operation of a vascular stent.

FIG. 2 is a closeup conceptual view of stent 24 as place after dilatation of occlusion 14 (not shown). Stent 24 is generally cylindrical in shape having an inner lumen 26. Preferably, stent 24 is fabricated from thin, biocompatible tubing of stainless steel, titanium, or Nitinol. For coronary applications, stent 24 has a length of several millimeters to about one centimeter. A pattern (not shown in FIG. 2) is machined in the wall of stent 24 as described below. Stent 24 has an outside diameter which is sized to snugly fit within the inner lumen of coronary artery 16 after dilatation.

Figure 3A:
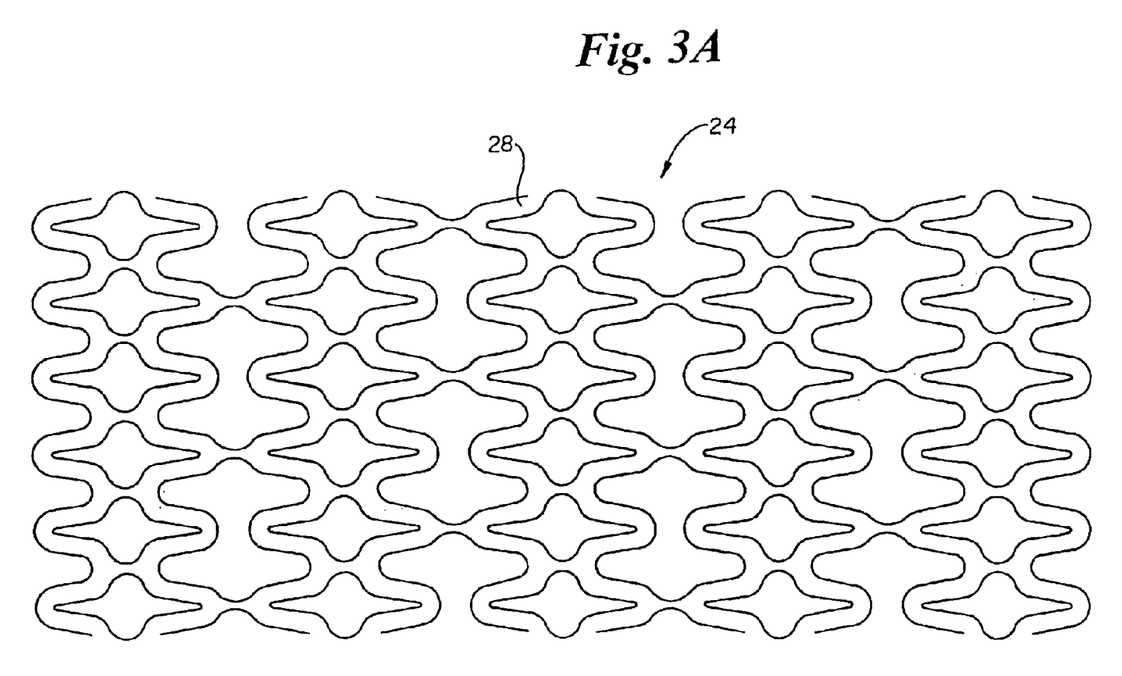
FIG. 3A is a closeup view conceptually showing a stent machined into a mesh-like pattern.

FIG. 3A is a close-up view of stent 24 as machined into a mesh-like pattern. Such machining removes much of the mass from the implanted stent. The mesh-like pattern increases flexibility of the stent and improves perfusion to the endothelial cells at the inside surface of the vessel wall.

Stent element 28 appears as a portion of the generally cylindrical surface of stent 24. Stent element 28 has a generally flat outer surface and a generally flat inner surface. Stent element 28 is preferably recessed in accordance with one of the embodiments of the present invention as described below in detail.

Figure 3B:
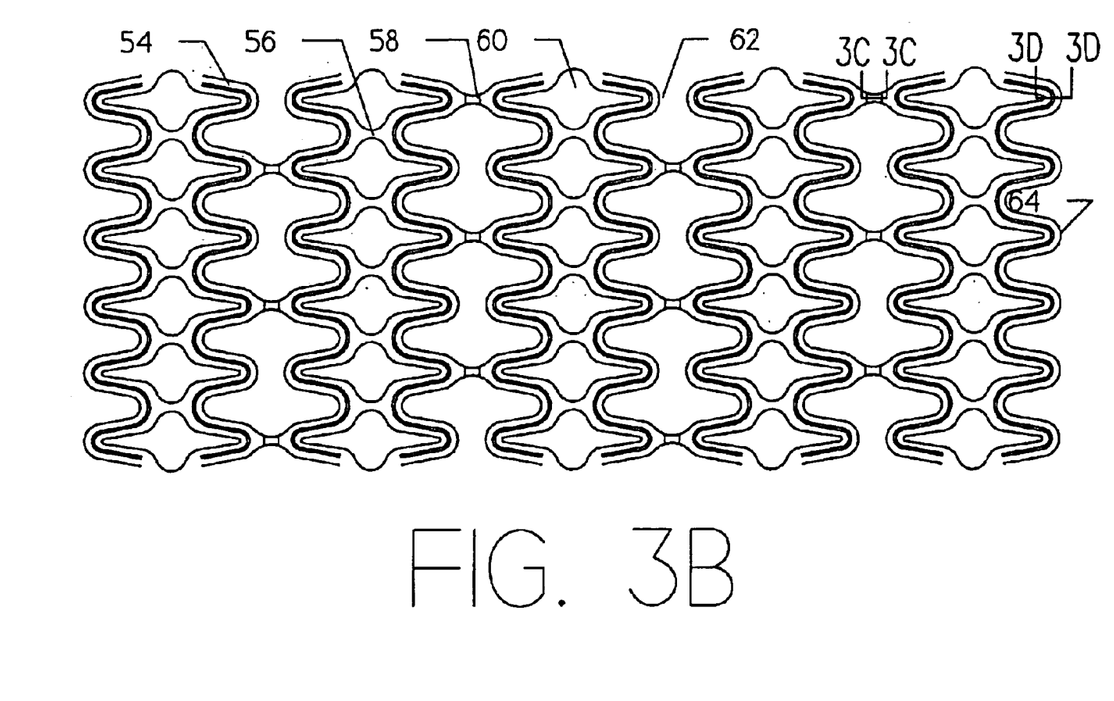
FIG. 3B is a closeup view of the mesh-like stent further machined with the channels of the present invention.

FIG. 3B is a closeup view of the mesh-like stent of FIG. 3A further machined to include pockets or channels in accordance with the present invention. As can be seen, the basic structure of the mesh-like pattern is a plurality of cells 60 interconnected to provide the desired size. Each cell 60 contains strut 54 and internal radial arc 62. The cells are connected via connecting bridge 56. Articulated bridge 58 is further machined as described in more detail below to enhance differential flexibility. The ends of stent 24 are defined by a plurality of end radial arcs 64. Section 3D—3D provides a closeup (see FIG. 3D) of a machined channel. Section 3C—3C provides a closeup (see FIG. 3C) of a machined articulated bridge.

Figure 3C:
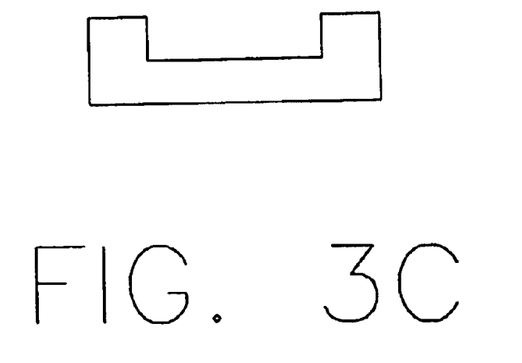
FIG. 3C is a closeup view of a section of the stent of FIG. 3B as seen along line 3C—3C.

FIG. 3C is a closeup of a machined articulatd bridge as indicated by 3C—3C in FIG. 3B.

Figure 3D:
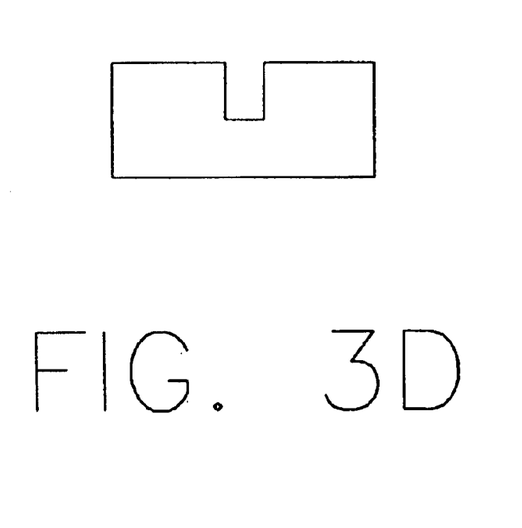
FIG. 3D is a closeup view of a section of the stent of FIG. 3B as seen along line 3D—3D.

FIG. 3D is a closeup of a machined channel as indicated by 3D—3D in FIG. 3B.

Figure 4:
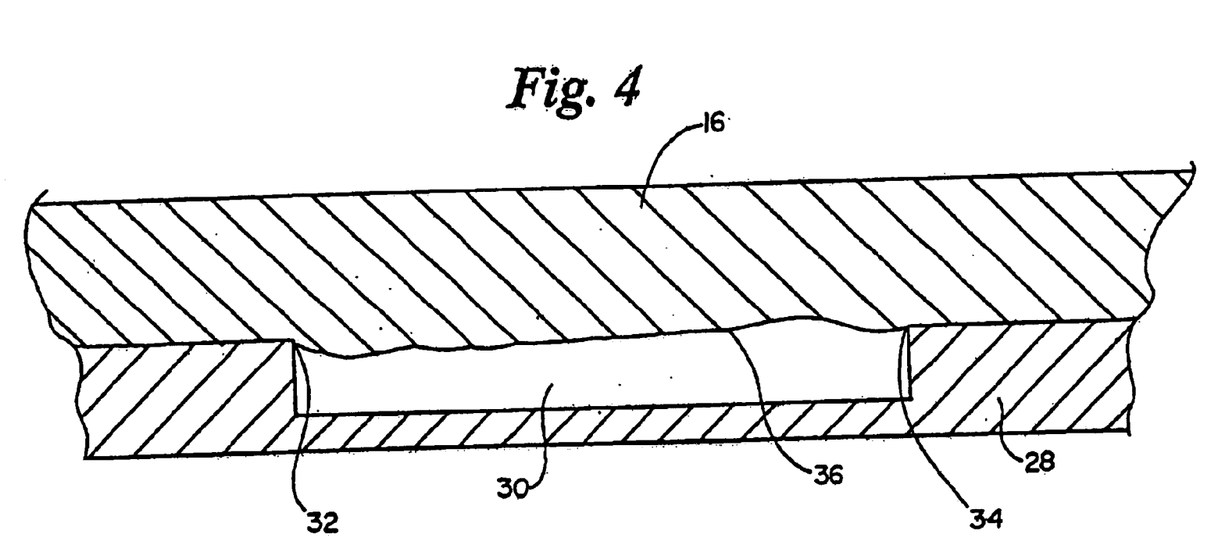
FIG. 4 is a very close up sectioned view of the contact between the longitudinally channeled stent element and the vessel wall.

FIG. 4 is a very close-up sectioned view of stent element 28 (the remainder of stent 24 is not shown for clarity) as chronically implanted. As shown, stent element 28 is channeled in the longitudinal direction (i.e., direction of blood flow). Channel 30 faces outwardly, as shown. This permits greater perfusion of surface 36 of coronary artery 16. Furthermore, edges 32 and 34 tend, to prevent inadvertent repositioning during chronic implantation.

Figure 5:
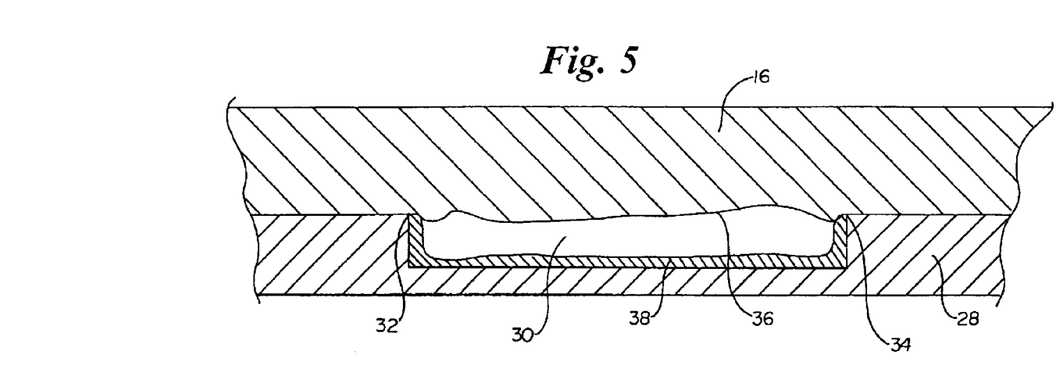
FIG. 5 is a view similar to FIG. 4 having a medication for chronic therapy.
Figure 6:
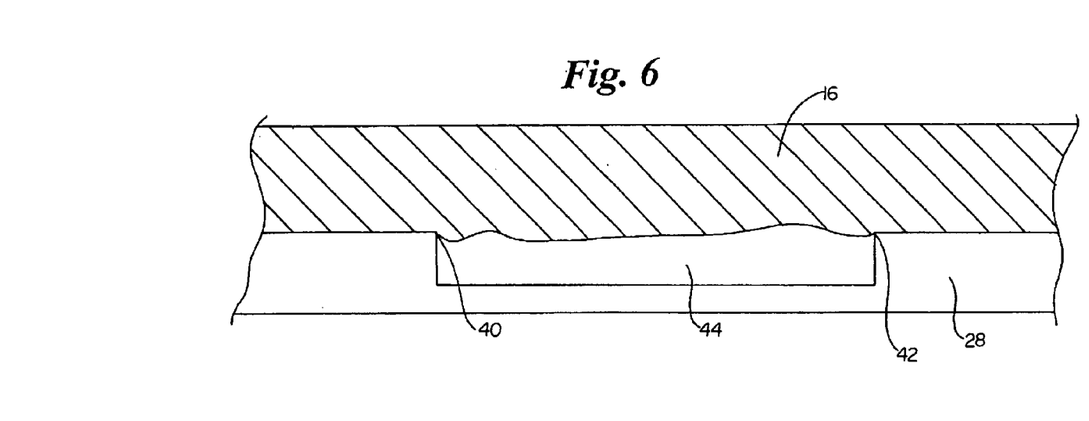
FIG. 6 is a very close up view of the contact between the laterally channeled stent element and the vessel wall.

FIG. 5 is a view similar to that shown in FIG. 6 with the addition of medication 38 within channel 30. Medication 38 is typically an anti-clotting agent, such as TPA, or an anti-irritant, such as a suitable steroid. The placement of medication 38 within channel 30 enhances chronic dispersion of the drug.

FIG. 6 is a view similar to FIG. 4, in which stent element 28 (the remainder of stent 24 is not shown for clarity) is channeled laterally (i.e., perpendicular to the direction of blood flow). Channel 44 is formed in the same manner as channel 30 (see also FIG. 4), but it is machined perpendicularly. Channel 44, edge 40, and edge 42 function in the same manner as channel 30, edge 32, and edge 34.

Figure 7:
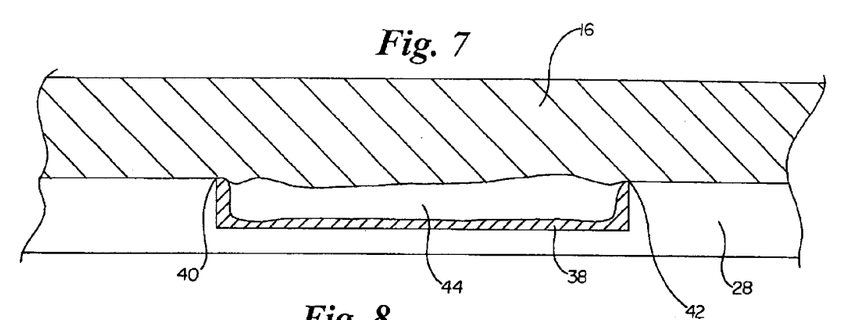
FIG. 7 is a view similar to FIG. 6 having a medication for chronic therapy.

FIG. 7 is a view similar to FIG. 6 wherein channel 44 contains medication 38. This embodiment functions similar to the embodiment of FIG. 5.

Figure 8:
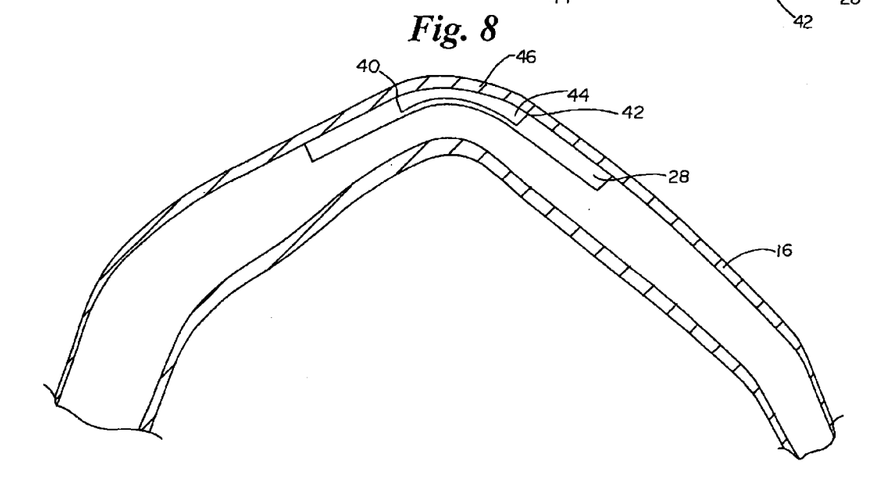
FIG. 8 is a very close up view of the contact between the laterally channeled stent element and the vessel wall showing differential flexibility around a bend in the vessel wall.

FIG. 8 is a view similar to FIG. 6 wherein channel 44 is utilized to provide differential flexibility to stent element 28. This differential flexibility is important in accommodating bend 46 of vessel 16. This differential flexibility also assists in resisting inadvertent repositioning.

Figure 9:
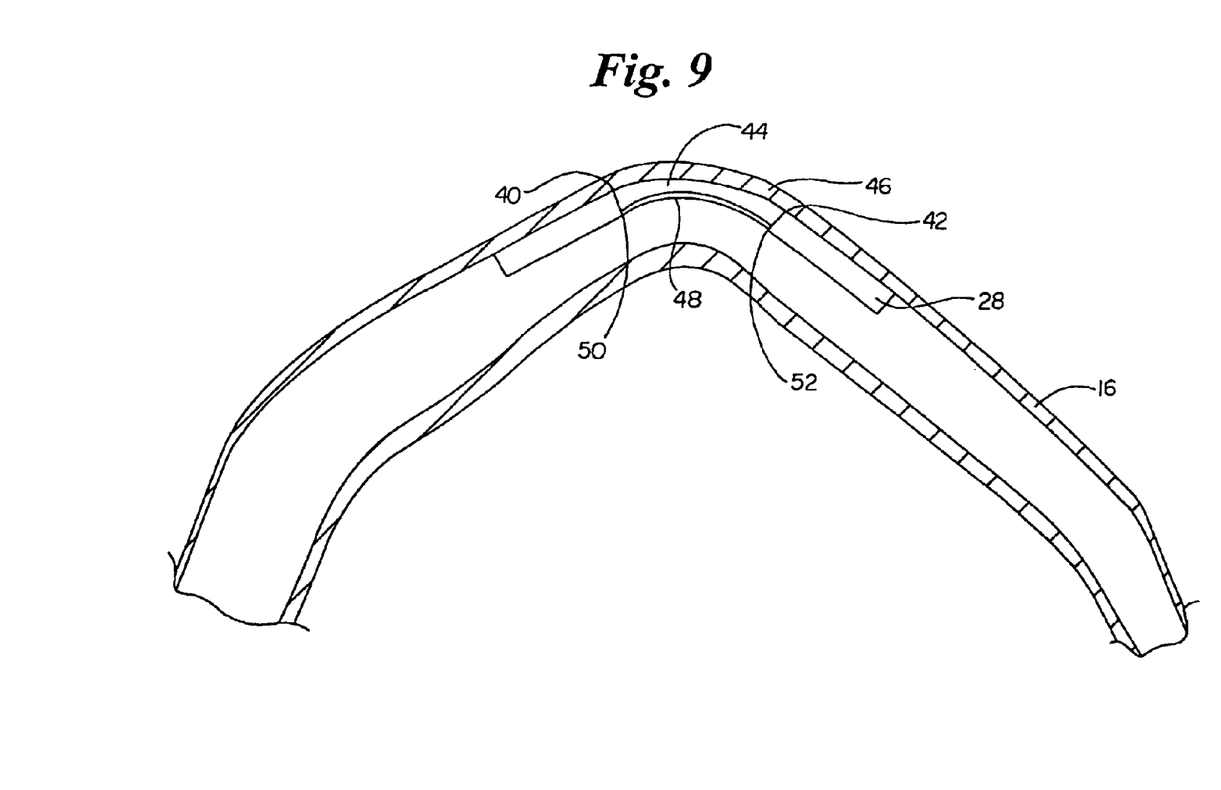
FIG. 9 is a view similar to that of FIG. 8 wherein the stent element has been machined into an articulated bridge.

FIG. 9 is a view similar to FIG. 8 wherein channel 40 has been machined deeply into stent element 28 and wherein the thin region 48 in stent element 28 imparts a particular articulation in stent 24.

Having thus described the preferred embodiments of the present invention, those of skill in the art will readily appreciate that the teachings found herein may be applied to yet other embodiments within the scope of the claims hereto attached.

What is claimed is:

1. In a vascular stent having a generally cylindrical shape with an outer surface and an inner surface, the improvement comprising:

a matrix formed from a plurality of elongated struts and including a plurality of densely populated, generally uniformly repeating channels occupying substantially fully said outer surface, each channel extending continuously longitudinally in a corresponding strut; and a medication contained within said plurality of channels.

2. The improvement according claim 1 wherein said plurality of channels extend generally in a longitudinal direction of said cylindrical shape.

3. The improvement according to claim 1 wherein said plurality of channels extend in a radial direction with regard to said cylindrical shape.

4. The improvement according to claim 1 wherein said stent is machined to produce a pattern having a plurality of stent elements.

5. The improvement according to claim 4 wherein said plurality of channels is machined into said plurality of stent elements.

6. The improvement according to claim 1 wherein each have said plurality of channels is outwardly concave.

7. An apparatus, comprising:
  a. A vascular stent having a generally cylindrical shape and having an outer surface;
  b. A matrix formed from a plurality of elongated struts and including a plurality of densely populated, generally uniformly repeating channels covering substantially fully said outer surface, each channel extending continuously longitudinally in a corresponding strut; and
  c. A medication contained within said plurality of channels.

8. An apparatus according to claim 7 wherein said vascular stent further comprises a plurality of stent elements.

9. An apparatus according to claim 8 wherein said plurality of channels is located on said plurality of stent elements.

10. An apparatus according to claim 9 wherein said plurality of channels extend in a direction generally parallel to said cylindrical shape.

11. An apparatus according to claim 9 wherein said plurality of channels extend in a radial direction with regard to said cylindrical shape.

12. An apparatus according to claim 7 wherein each of said plurality of channels is outwardly concave.

13. An apparatus, comprising:
  a. Means for stenting a vessel, said means for stenting having an outer surface and a longitudinal axis;
  b. Means located on said outer surface for enhancing perfusion, said means for enhancing perfusion comprising a matrix of closely spaced elongated struts defining repeating patterns of channels wherein each channel extends continuously longitudinally in a corresponding strut; and
  c. a medication received within said channels.

14. An apparatus according to claim 13, further comprising means responsively coupled to said outer surface for imparting differential flexibility.

15. An apparatus according to claim 14 wherein said channels are located on said stent element in a generally parallel direction to said longitudinal axis.

16. An apparatus according to claim 14 wherein said channels are located on said stent element in a generally perpendicular direction to said longitudinal axis.

17. An apparatus according to claim 13 wherein each of said channels is outwardly concave.

* * * * *